(12) United States Patent
Chang

(10) Patent No.: US 8,047,684 B2
(45) Date of Patent: Nov. 1, 2011

(54) LED ILLUMINATOR WITH IMPROVED BEAM QUALITY

(75) Inventor: Byung J. Chang, Ann Arbor, MI (US)

(73) Assignee: General Scientific Corporation, Ann Arbor, MI (US)

( * ) Notice: Subject to any disclaimer, the term of this patent is extended or adjusted under 35 U.S.C. 154(b) by 0 days.

(21) Appl. No.: 12/623,470

(22) Filed: Nov. 23, 2009

(65) Prior Publication Data

US 2011/0122598 A1 May 26, 2011

(51) Int. Cl.
*F21V 5/00* (2006.01)
(52) U.S. Cl. ......... 362/268; 362/271; 362/273; 362/331
(58) Field of Classification Search .................. 362/268, 362/270, 271, 273, 277, 331, 335, 336
See application file for complete search history.

(56) References Cited

U.S. PATENT DOCUMENTS

| 3,745,993 | A | | 7/1973 | Feinbloom |
| 5,042,048 | A | * | 8/1991 | Meyer ........................... 372/108 |
| 5,924,234 | A | * | 7/1999 | Bindon et al. .................. 42/123 |
| 2007/0217198 | A1 | * | 9/2007 | Alessio ......................... 362/268 |
| 2008/0019011 | A1 | * | 1/2008 | Krneta et al. ................. 359/641 |
| 2009/0059095 | A1 | * | 3/2009 | Hall et al. ..................... 348/744 |

* cited by examiner

*Primary Examiner* — Laura Tso
(74) *Attorney, Agent, or Firm* — Gifford, Krass, Sprinkle, Anderson & Citkowski, P.C.

(57) ABSTRACT

An improved illuminator with an adjustable beam pattern to be worn by medical and dental professionals includes a housing, a light-emitting diode (LED) disposed in the housing outputting light through a distal opening in the housing, an achromatic doublet lens mounted in the opening in the housing, and a singlet lens disposed between the LED and the achromatic lens. The distance between the singlet lens and the doublet lens may be adjustable, and/or distance between the LED and the singlet lens may be adjustable, through a threaded connections, for example.

18 Claims, 3 Drawing Sheets

LED ILLUMINATOR WITH IMPROVED BEAM QUALITY

FIELD OF THE INVENTION

This invention relates generally to illuminators of the type worn by medical and dental professionals and, in particular, to an LED illuminator with multiple optical elements to improve beam quality

BACKGROUND OF THE INVENTION

The light generated by existing light-emitting diode (LED) illuminators is quite poor. Current illuminators of this kind use reflecting optical elements or singlet or multiple lenses with reflecting optical elements. An example is shown in U.S. Pat. No. 3,745,993 entitled "Surgical Headlight." Although this design discloses an achromatic lens, the light delivered to it from an optical fiber is reflected off of a mirror. As such, this and other existing configurations exhibit poor light uniformity and/or unacceptable color separation at the edge of beam.

SUMMARY OF INVENTION

This invention improves upon existing designs by providing an illuminator with an adjustable beam pattern to be worn by medical and dental professionals, comprising:

The preferred embodiment includes a housing, a light-emitting diode (LED) disposed in the housing outputting light through a distal opening in the housing, an achromatic doublet lens mounted in the opening in the housing, and a singlet lens disposed between the LED and the achromatic lens.

The distance between the singlet lens and the doublet lens may be adjustable, and/or distance between the LED and the singlet lens may be adjustable, through a threaded connections, for example.

DETAILED DESCRIPTION OF THE INVENTION

Figure 1:
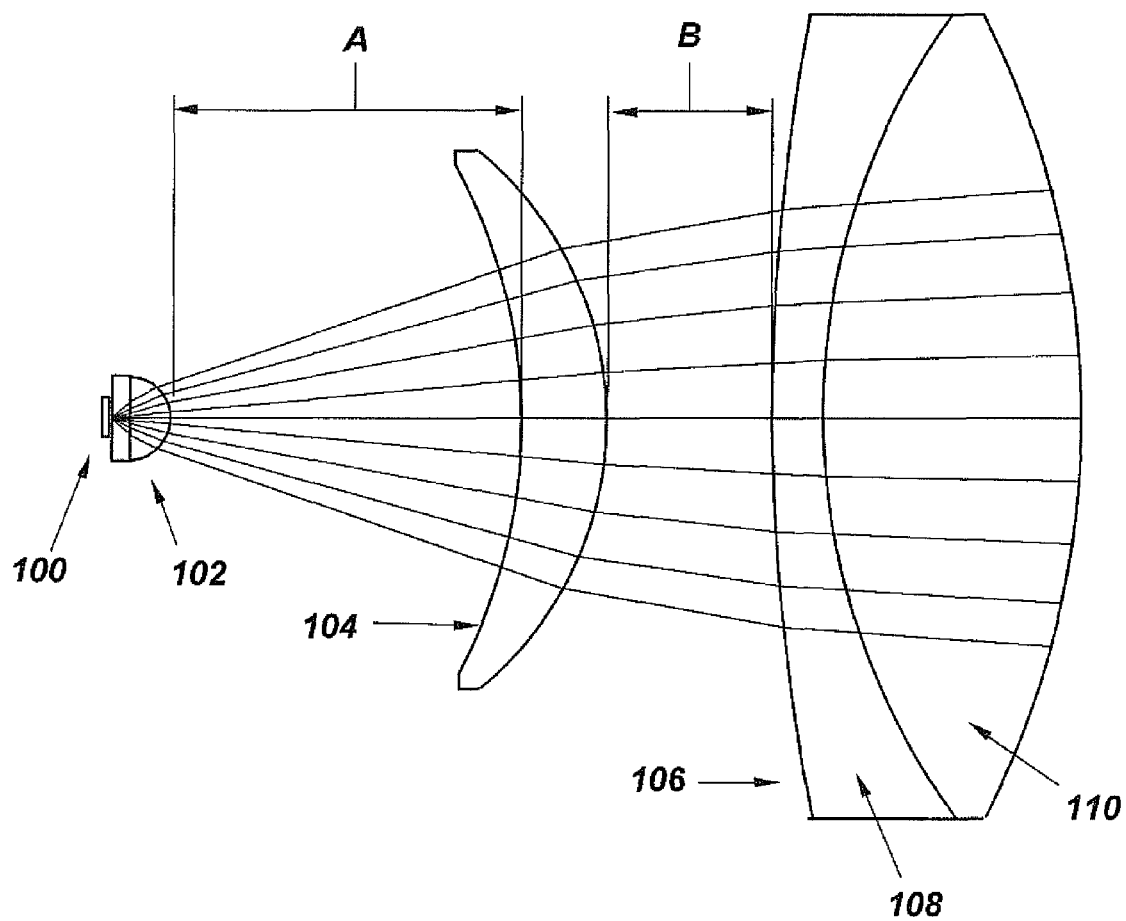
FIG. 1 is a cross section of a preferred embodiment of the invention.
Figure 2:
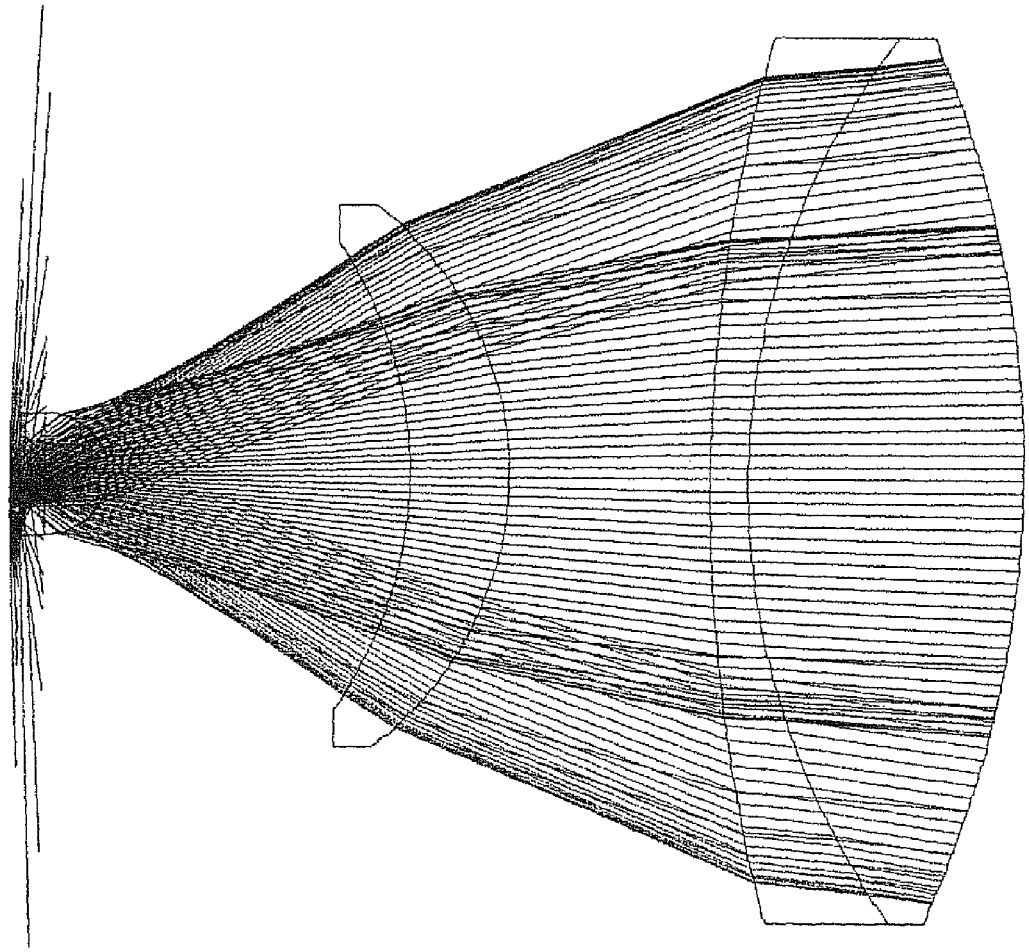
FIG. 2 is a ray-tracing diagram of the preferred embodiment.

This invention resides in an LED illuminator with multiple optical elements to improve beam quality. As shown in FIG. 1, the preferred embodiment uses one singlet lens 104 and one achromatic doublet lens 106 (made with one positive and one negative lens 108, 110). The system is based upon a high-intensity white-emitting LED 100 including an integral lens 102, which may be spherical.

One or both distances A, B can be either fixed or adjustable for beam pattern or different applications. For typical headlamp applications, A may be on the order of 6 mm, adjustable between 4 to 11 mm, while B may be on the order of 4 mm, adjustable between 2 to 6 mm or thereabouts. The diameter of the singlet 104 may be in the range of 7 to 10 mm, whereas the achromatic doublet lens 106 will be on the order of 17 to 20 mm, again for typical headlamp applications. The radius of the LED lens may be 2.5 mm+/−0.5 mm.

Figure 3:
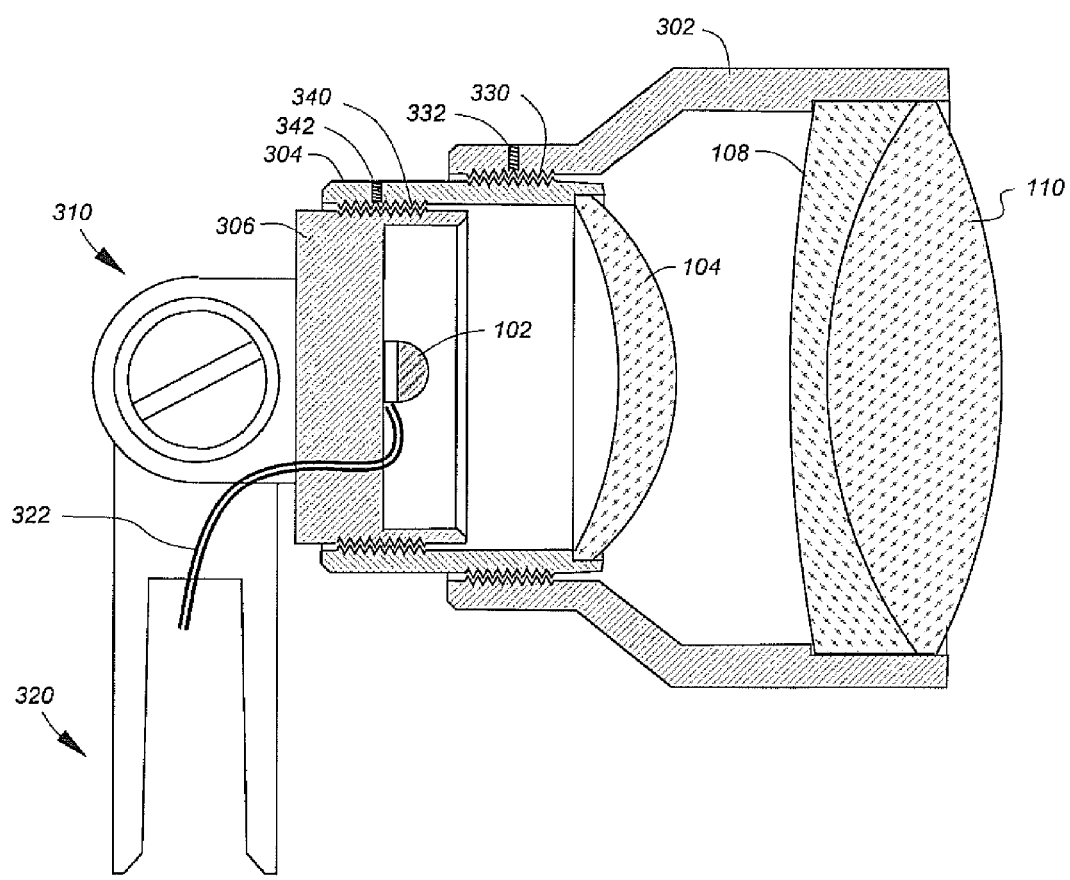
FIG. 3 is a drawing of a housing applicable to the present invention.

FIG. 3 shows a suitable housing for the preferred optical assembly. Doublet 108, 110, is disposed in a housing 302; singlet 104 is disposed in housing 304, and LED 102 is mounted within housing 306. The housings are coupled via threaded connections 330, 340, with set screws 332, 342 and/or an adhesive being used to fix the relative positions. If one or both distances are permanently fixed, one or both of the threaded connections 330, 340 may be eliminated, simplifying the housing overall.

The base housing 306 is preferably coupled to a clip-on type connector 320 through hinge 310. The invention is not limited in this regard insofar as other attachment mechanisms may be used. Any materials such as plastic, metal (i.e., aluminum) may be used for the housing pieces. Heat vents or sinks (not shown) may also be provided. The cord for the LED is depicted at 322.

I claim:

1. An illuminator of the type worn by medical and dental professionals, comprising:
    a housing;
    a light-emitting diode (LED) disposed in the housing outputting light through a distal opening in the housing;
    an achromatic doublet lens mounted in the opening in the housing;
    a singlet lens disposed between the LED and the achromatic lens; and
    an attachment mechanism coupled to the housing enabling the illuminator to be worn as a headlamp.

2. The illuminator of claim 1, wherein the distance between the singlet lens and the doublet lens is adjustable through a threaded connection.

3. The illuminator of claim 1, wherein the distance between the LED and the singlet lens is adjustable through a threaded connection.

4. The illuminator of claim 1, wherein:
    the distance between the singlet lens and the doublet lens is adjustable through a threaded connection; and
    the distance between the LED and the singlet lens is adjustable through a different threaded connection.

5. The illuminator of claim 1, wherein the attachment mechanism is a clip-on connector.

6. The illuminator of claim 1, wherein the LED is a white LED.

7. The illuminator of claim 1, wherein the LED includes an integral lens.

8. The illuminator of claim 1, wherein the LED includes an integral spherical lens.

9. The illuminator of claim 1, wherein the output light has a non-collimated, divergent beam pattern.

10. The illuminator of claim 1, wherein:
    the output light has a non-collimated, divergent beam pattern; and
    the beam pattern is adjustable through movement of one or both of the lenses.

11. An illuminator of the type worn by medical and dental professionals, comprising:
    a housing having a distal opening;
    a light-emitting diode (LED) disposed in the housing;
    an achromatic doublet lens mounted in the distal opening;
    a singlet lens disposed in the housing between the LED and the achromatic lens;
    wherein the lenses output a non-collimated, divergent beam pattern; and
    an attachment mechanism coupled to the housing enabling the illuminator to be worn as a headlamp.

12. The illuminator of claim 11, wherein the distance between the singlet lens and the doublet lens is adjustable through a threaded connection.

13. The illuminator of claim 11, wherein the distance between the LED and the singlet lens is adjustable through a threaded connection.

14. The illuminator of claim 11, wherein:
- the distance between the singlet lens and the doublet lens is adjustable through a threaded connection; and
- the distance between the LED and the singlet lens is adjustable through a different threaded connection.

15. The illuminator of claim 11, wherein the attachment mechanism is a clip-on connector.

16. The illuminator of claim 11, wherein the LED is a white LED.

17. The illuminator of claim 11, wherein the LED includes an integral lens.

18. The illuminator of claim 11, wherein the LED includes an integral spherical lens.

* * * * *